United States Patent [19]

Hanamura et al.

[11] 4,235,540
[45] Nov. 25, 1980

[54] EYE FUNDUS CAMERA HAVING VARIABLE POWER PHOTOGRAPHING OPTICAL SYSTEM

[75] Inventors: Yoshihiko Hanamura; Schinichi Nishimura, both of Tokyo, Japan

[73] Assignee: Tokyo Kogaku Kikai Kabushiki Kaisha, Tokyo, Japan

[21] Appl. No.: 35,804

[22] Filed: May 4, 1979

[30] Foreign Application Priority Data

May 10, 1978 [JP] Japan .................................. 53-55189
May 10, 1978 [JP] Japan .................................. 53-55190
May 10, 1978 [JP] Japan .................................. 53-55191

[51] Int. Cl.³ .............................................. A61B 3/14
[52] U.S. Cl. ......................................... 354/62; 351/7; 354/197
[58] Field of Search .......................... 351/6, 7, 10, 11; 350/19, 39; 354/62, 78, 197

[56] References Cited

U.S. PATENT DOCUMENTS

| 1,741,526 | 12/1929 | Kuhl ........................................ 351/7 |
| 3,535,027 | 10/1970 | Littmann et al. ...................... 351/14 |
| 3,652,153 | 3/1972 | Gambs .................................... 351/14 |
| 3,896,466 | 7/1975 | Korpert ................................. 354/196 |
| 3,944,342 | 3/1976 | Martinez .............................. 351/7 X |

*Primary Examiner*—John Gonzales
*Attorney, Agent, or Firm*—Stevens, Davis, Miller & Mosher

[57] ABSTRACT

Eye fundus camera including a photographing optical system comprised of an objective lens, an imaging lens and a magnification power changing lens device. The power changing lens device is movable in axial direction for effecting focusing.

4 Claims, 7 Drawing Figures

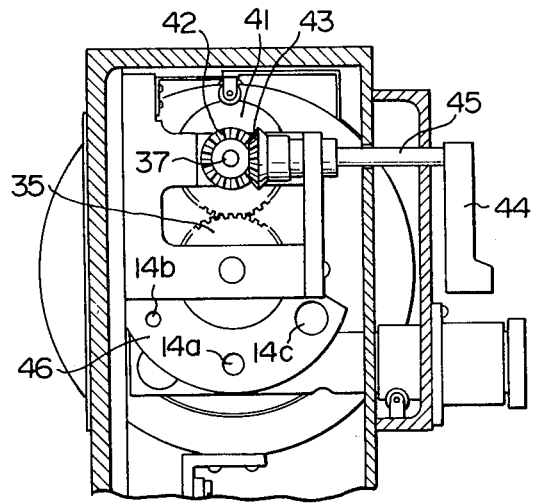
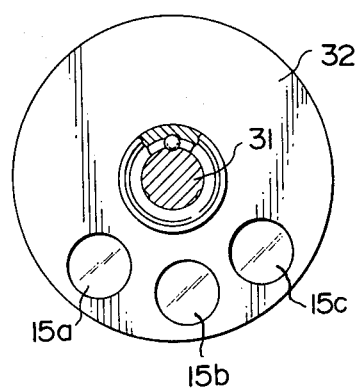
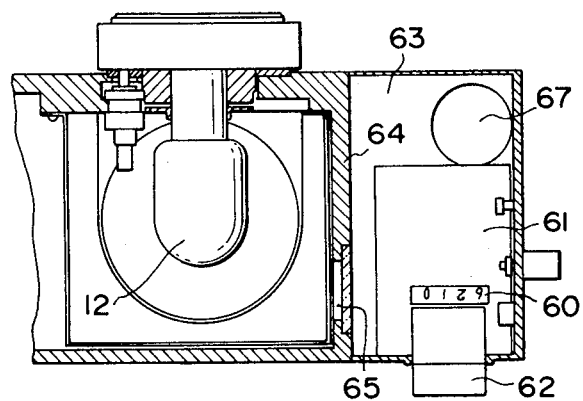

EYE FUNDUS CAMERA HAVING VARIABLE POWER PHOTOGRAPHING OPTICAL SYSTEM

The present invention relates to eye fundus cameras and more particularly to eye fundus cameras having optical systems of variable magnification power.

In eye fundus cameras, in order to provide a change in magnification power of photographing system, a zoom lens may be included in the photographing optical system. Alternatively, a plurality of lenses of different magnification powers may be mounted on a member which is rotatable about an axis parallel with the photographing optical axis so that the lenses can alternately be inserted into the photographing optical path. In this type of variable magnification eye fundus cameras, focusing may be performed through an axial movement of the imaging lens. However, this type of focusing means is disadvantageous in that it requires a substantial distance of axial displacement of the imaging lens so that the camera becomes unavoidably bulky. The focusing may alternatively be performed through a displacement of the photographing film plane, however, inconveniencies will be encountered in this system because the eyepiece is simultaneously displaced upon the focusing operation.

It is therefore an object of the present invention to provide a variable magnification eye fundus camera in which the aforementioned problems can be overcome.

Another object of the present invention is to provide a magnification power changing device in an eye fundus camera which allows a compact design of the camera and does not produce any displacement of the eye piece upon focusing operation.

A further object of the present invention is to provide a variable magnification eye fundus camera having means for adjusting the photographing aperture in accordance with the magnification power of the photographing optical system.

Still further object of the present invention is to provide means for restricting illuminating light under a high power magnification for eliminating or at least decreasing adverse effects of surplus light being reflected in the body of the camera.

According to the present invention, the above and other objects can be accomplished by an eye fundus camera having a photographing optical system having a photographing optical axis and comprised of objective lens means, imaging lens means and magnification power changing lens means positioned between the objective lens means and the imaging lens means, said magnification power changing lens means being movable along the optical axis of the photographing optical system for focusing. In a preferable aspect of the present invention, the magnification power changing lens means comprises a plurality of lenses having different focal distance, said lenses being mounted on a member which is rotatable about an axis parallel with the photographing optical axis so that a desired one of the lenses can be placed in the photographing optical path through rotation of the rotatable member. The rotatable member is mounted for movement along the photographing optical axis to thereby effect focusing. The objective lens means and the power changing lens means may be so designed that the image of the pupil of the patient's eye is produced substantially at the same position even when the magnification power is changed.

According to the feature of the present invention, the magnification power changing lens means is used for focusing so that the distance of the axial movement of the lens means is smaller than in an arrangement wherein the focusing is performed through an axial movement of the imaging lens means. Thus, it is possible to make the optical system shorter than in a conventional design. Since the photographing film plane can be maintained stationary, the eye piece can also be maintained against axial displacement.

It may be possible to effect a magnification power change at the imaging lens means in the photographing optical system, however, this arrangement is disadvantageous as compared with the arrangement in accordance with the present invention in that an increased number of lenses are required and the lens system becomes large accordingly.

According to a further aspect of the present invention, the photographing optical system is provided with adjustable aperture means which is interconnected with the magnification power changing lens means so that the aperture means is adjusted in accordance with the magnification power of the lens means. The adjustable aperture means may be comprised of a plurality of apertures of different diameters formed in a rotatable member which is interconnected with the magnification power changing lens means so that appropriate one of the apertures is inserted into the photographing optical path upon adjustment of the magnification power changing lens means.

According to a further feature of the present invention, the eye fundus camera has an illumination system which is provided with adjustable aperture means interconnected with magnification power changing lens means so that the illumination aperture is changed in accordance with the magnification power of the photographing optical system.

The above and other objects and features of the present invention will become apparent from th following descriptions of preferred embodiments taking reference to the accompanying drawings, in which;

FIG. 3 is a sectional view taken substantially along the line III—III in FIG. 2;

FIG. 4 is a sectional view taken substantially along the line IV—IV in FIG. 2;

FIG. 6 is a sectional view taken substantially along the line VI—VI in FIG. 2; and, FIG. 7 is a view showing the illumination aperture adjusting arrangement in accordance with one embodiment of the present invention.

Figure 1:
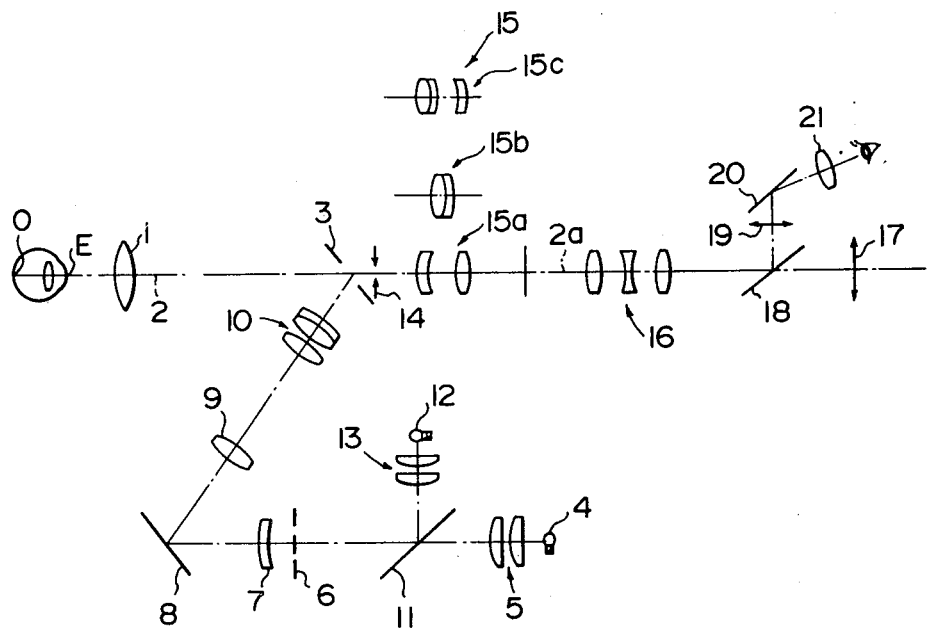
FIG. 1 is a diagrammatical view of the optical system of an eye fundus camera in accordance with one embodiment of the present invention.

Referring now to the drawings, particularly to FIG. 1, the optical system shown therein includes a nonspherical objective lens 1 which is adapted to be placed against an eye E to be inspected. The objective lens 1 has an optical axis 2 on which an apertured mirror 3 is located in conjugate with the pupil of the patient's eye E with respect to the objective lens 1.

The optical system includes an illuminating system comprised of a photographing xenon lamp 4 from which the light is passed through a condenser lens 5, a ring-shaped aperture 6 and a lens 7 to a mirror 8 to be reflected thereby. The light reflected by the mirror 8 is then passed through lenses 9 and 10 to the apertured mirror 3 which reflects the light toward the objective lens 1. The light is then passed through the pupil of the patient's eye E to the fundus O. Between the condenser lens 5 and the ring-shaped aperture 6, there is located a half-transparent mirror and a tungsten lamp 12 is provided so that the light therefrom is passed through a condenser lens 13 to the mirror 11 to be reflected thereby toward the aperture 6.

The photographing optical system is comprised of an aperture 14 which is located behind the apertured mirror 3 substantially in conjugate with the pupil of the patient's eye E with respect to the objective lens 1, a magnification power changing and focusing lens system 15 and an imaging lens system 16 which are provided behind the aperture 14 along a photographing optical axis 2a. The light reflected at the eye fundus O is therefore passed the aperture 14, the lens system 15 and the lens system 16 to produce an image of the eye fundus on a photographing film plane 17.

The magnification power changing and focusing lens system 15 is comprised of a plurality sets of power changing lenses 15a, 15b and 15c and a desired one of the lenses is inserted into the photographing optical path. It is easy to mount the lenses 15a, 15b and 15c in such a manner that they can be alternately inserted into the photographing optical path substantially at the same location so that there is no change in the eye point upon a power changing operation. The lens system 15 is further movable along the optical axis 2a for the purpose of focusing.

In front of the film plane 17, there is disposed a retractable mirror 18 which functions in the illustrated position to reflect the light through the imaging lens system 16 to an image plane 19 so that the image on the plane 19 is observed through a mirror 20 and an eye lens 21. The retractable mirror 18 may be substituted by a half-transparent mirror or a prism.

Referring now to FIGS. 2 through 5, the eye fundus camera shown therein includes a housing 30 which contains the aforedescribed illuminating and photographing optical systems. In these drawings, corresponding parts are therefore shown by the same reference numerals as in FIG. 1.

The magnification power changing and focusing lens system 15 includes a rotatable member 32 which is mounted on a rotatable shaft 31 to rotate therewith but for axial sliding movement with respect thereto. The member 32 carries three sets of magnification power changing lenses 15a, 15b and 15c. The rotatable shaft 31 is journalled at the opposite ends by means of bearings 33 and 34 and has a gear 35 secured to one end thereof. Adjacent to the gear 35, the shaft 31 carries a gear 36 which is freely rotatable on the shaft. The gear 36 is in meshing engagement with a gear 38 which is secured to an actuating shaft 37 so that the gear 36 can be rotated by actuating the shaft 37 through a lever 39 provided on the shaft 37. The gear 36 carries correcting lenses 40 so that appropriate one of the lenses 40 can be inserted into the photographing path in accordance with the visual power of the operator.

The gear 35 which is secured to the rotatable shaft 31 is in meshing engagement with a gear 41 rotatably mounted on the actuating shaft 37. A bevel gear 42 is secured to the gear 41 and in meshing engagement with a bevel gear 43 as shown in FIG. 3. The gear 43 is secured to a magnification power changing shaft 45 which is adapted to be actuated by a handle 44. It is therefore possible to rotate the member 32 through the handle 44 so that a desired one of the lenses 15a, 15b and 15c is inserted into the photographing optical path.

The gear 35 carries an aperture plate 46 which is secured thereto and provides the aforementioned aperture device 14. The plate 46 is formed with a plurality of apertures 14a, 14b and 14c which are adapted to be alternately inserted into the photographing optical path in accordance with the magnification power changing lens. The arrangement is advantageous in that an appropriate aperture adjustment can be accomplished in accordance with the power changing lens or the magnification power simultaneously with the power changing operation so that it is possible to maintain the brightness of the field substantially constant. Further, the quality of the picture can be improved because the aperture plate 46 blocks surplus light which may otherwise be reflected in th camera and enter the photographing optical path possibly causing flare or ghost images.

The rotatable member 32 is formed with an annular flange 32a on which a focusing ring member 48 is mounted through a ball bearing 47. The ring member 48 is secured to a rack member 49 which is formed with a rack 49a and carried by a guide member 50 for movement in an axial direction. The rack 49a on the member 49 is engaged with a pinion 53 provided on a focusing shaft 52 which is rotated by means of a focusing knob 51. It should therefore be noted that, through an actuation of the focusing knob 51, the rack member 49 is moved in the axial direction to thereby shift the rotatable member 32 through the ring member 48 in the axial direction on the shaft 31 to perform focusing.

Figure 2:
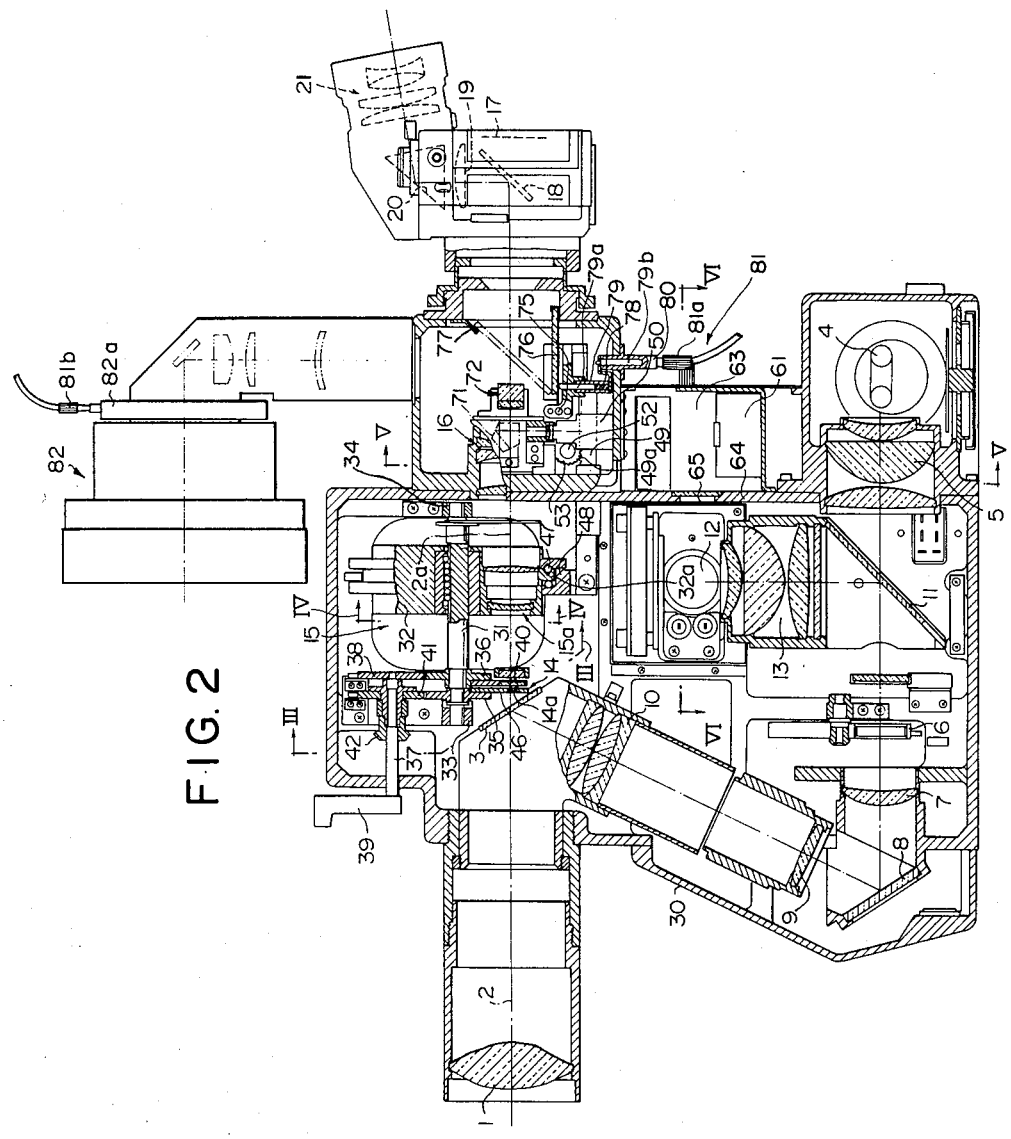
FIG. 2 is a sectional view of the eye fundus camera having the optical system shown in FIG. 1.
Figure 5:
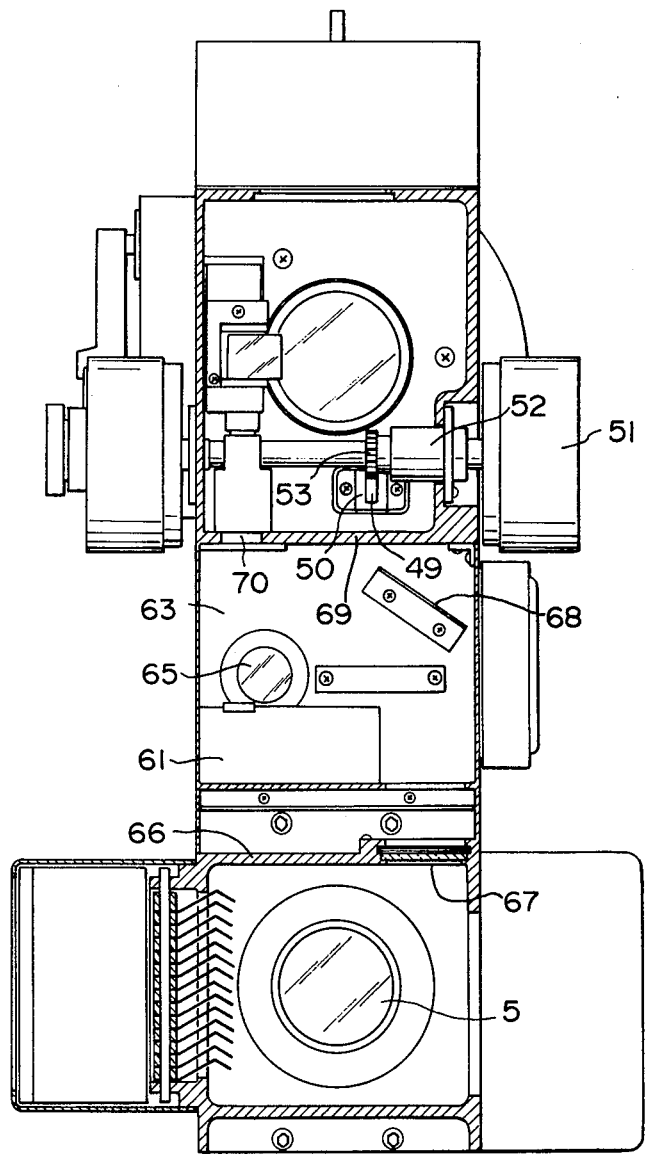
FIG. 5 is a sectional view taken substantially along the line V—V in FIG. 2.

The eye fundus camera shown therein is further provided with a data projecting system which comprises, as shown in FIG. 6, a counter 61 having a display window 60 for showing a data identification number and a data card 62 adapted to be placed on the counter 61. As shown in FIGS. 2, 5 and 6, the counter 61 is disposed in a compartment 63 which is provided above the photographing lamp 4 and behind the observing lamp 12. The compartment 63 is separated from a compartment wherein the lamp 12 is disposed by means of a wall 64 which is provided with an opening so that the display window 60 on the counter 61 and the data card 62 are illuminated by the light from the lamp 12 through the opening 65.

The compartment 63 is further separated from a compartment wherein the lamp 4 is disposed by means of a wall 66 which is formed with an opening 67. Thus, the light from the lamp 4 can illuminate the compartment 63 through the opening 67. In the compartment 63, there is provided a mirror 68 which functions to reflect the light through the opening 67 toward the window 60 on the counter 61 and the data card 62.

A wall 69 is provided to define an upper confine of the compartment 63 and has an opening 70 which is located above the window 60 and the data card 62 so that the light therefrom is directed through the opening 70 to a side of the photographing optical axis. At the side of the optical axis, there is disposed a pentagonal prism 71 which reflects the light through the opening 70 rearwardly through an imaging lens 70 to a portion of the photographing film 17. The arrangement is advantageous in that the data projection can be performed by making use of a surplus light with the addition of only the reflecting prism and the lens. Further, the data projecting system can well be arranged in a space of a camera which is not normally utilized.

The illustrated eye fundus camera further includes a device for taking an instantaneous photograph. The device is comprised of a reflecting mirror 76 carried rotatably on a shaft 75 located beneath the photographing optical path. The mirror 76 is normally maintained under its own weight in a retracted or horizontal position as shown by solid lines in FIG. 2 so that does not disturb the photographing light bundle. However, it can be raised to a position shown by phantom lines in FIG. 2 to reflect the photographing light bundle upwards. A stopper 77 is provided for determining the raised position of the mirror 76.

Beneath the mirror 76, there is provided a mirror raising member 79 which comprises a mirror raising pin 79a biased upwardly by means of a spring 78. The mirror raising pin 79a has an actuating pin 79b which is received in a release adapter 80 connected with one lever 81a of a bifurcated shutter release 81 so that the mirror 76 is moved to the raised position until it abuts the stopper 77 when the shutter release 81 is actuated for photographing.

Above the housing 30, there is mounted an instantaneous photographing device 82 so that the light from the mirror 76 is directed to the photographing device 82. The device 82 has a shutter device 82a which is adapted to be released by the other lever 81b of the bifurcated release 81. In order to ensure that the mirror 76 is in the raised position without fail when the shutter device 82a is released, the lever 81a has a working stroke greater than that of the other lever 81b.

Figure 7:
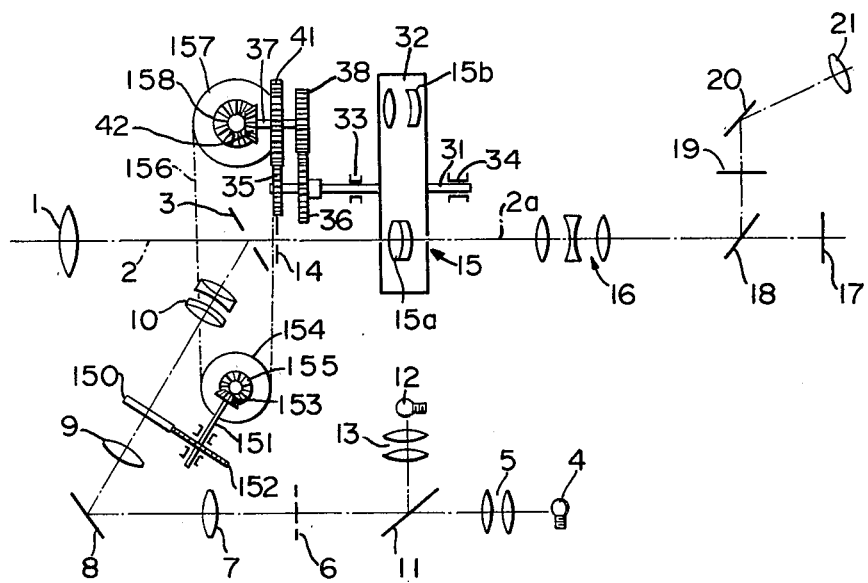

Referring now to FIG. 7, it will be noted that in the illuminating system there is provided an adjustable aperture such as a known type of iris diaphragm assembly 150 which is disposed between the lenses 9 and 10. The iris diaphragm assembly 150 is adapted to be actuated by means of a gear 152 on a shaft 151 so as to adjust the aperture diameter in the system. The shaft 151 has a bevel gear 153 secured to one end thereof and engaged with a bevel gear 155 which is secured to a pulley 154. The pulley 154 is in turn connected through a timing belt 156 with a pulley 157. A bevel gear 158 is secured to the pulley 157 and in meshing engagement with a suitable bevel gear on the shaft 37, for example, with the bevel gear 42 which has been described with reference to FIG. 2. It should therefore be noted that, when the rotatable member 32 is rotated to effect a change in the magnification power, the aperture diameter of the iris diaphragm assembly 150 is simultaneously adjusted to maintain the illumination field to a suitable range in accordance with magnification power of the photographing optical system. The arrangement is advantageous in that surplus illuminating light is blocked by the iris diaphragm assembly so that the quality of the picture can be improved.

The inventon has thus been shown and described with reference to specific arrangements, however, it should be noted that the invention is in no way limited to the details of the illustrated structures but changes and modifications may be made without departing from the scope of the appended claims.

We claim:

1. Eye fundus camera having a photographing optical system having a photographing optical axis and comprised of objective lens means, imaging lens means and magnification power changing lens means positioned between the objective lens means and the imaging lens means, said magnification power changing lens means being movable along the optical axis of the photographing optical system for focusing, said magnification power changing lens means comprising a plurality of lenses having different focal distances, said lenses being mounted on a member which is rotatable about an axis parallel with the photographing optical axis so that desired one of the lenses can be placed in the photographing optical path through rotation of the rotatable member.

2. Eye fundus camera in accordance with claim 1 in which said rotatable member is mounted for movement along the photographing optical axis to thereby effect focusing.

3. Eye fundus camera having a photographing optical system having a photographing optical axis and comprised of objective lens means, imaging lens means and magnification power changing lens means positioned between the objective lens means and the imaging lens means, said magnification power changing lens means being movable along the optical axis of the photographing optical system for focusing, adjustable aperture means which is interconnected with the magnification power changing lens means so that the aperture means is adjusted in accordance with the magnification power of the lens means, said adjustable aperture means being comprised of a plurality of apertures of different diameters formed in a rotatable member which is interconnected with the magnification power changing lens means so that appropriate one of the apertures is inserted into the photographing optical path upon adjustment of the magnification power changing lens means.

4. Eye fundus camera having a photographing optical system having a photographing optical axis and comprised of objective lens means, imaging lens means and magnification power changing lens means positioned between the objective lens means and the imaging lens means, said magnification power changing lens means being movable along the optical axis of the photographing optical system for focusing, and an illumination system which is provided with adjustable aperture means interconnected with said magnification power changing lens means so that the illumination aperture is changed in accordance with the magnification power of the photographing optical system.

* * * * *